(12) United States Patent
Maloney

(10) Patent No.: US 9,675,490 B2
(45) Date of Patent: Jun. 13, 2017

(54) ANKLE SUPPORTS

(71) Applicant: POD I.P. PTY LTD, Geelong, Victoria (AU)

(72) Inventor: Geoff Maloney, Geelong (AU)

(73) Assignee: POD GLOBAL IP PTY LTD, Victoria (AU)

( * ) Notice: Subject to any disclaimer, the term of this patent is extended or adjusted under 35 U.S.C. 154(b) by 260 days.

(21) Appl. No.: 14/408,882

(22) PCT Filed: Jun. 19, 2013

(86) PCT No.: PCT/AU2013/000655
§ 371 (c)(1),
(2) Date: Dec. 17, 2014

(87) PCT Pub. No.: WO2013/188915
PCT Pub. Date: Dec. 27, 2013

(65) Prior Publication Data
US 2015/0173930 A1    Jun. 25, 2015

(30) Foreign Application Priority Data

Jun. 19, 2012  (AU) .............................. 2012902571

(51) Int. Cl.
*A61F 5/01* (2006.01)
*A43B 7/20* (2006.01)
*A43B 1/00* (2006.01)

(52) U.S. Cl.
CPC .......... *A61F 5/0127* (2013.01); *A43B 1/0081* (2013.01); *A43B 7/20* (2013.01); *A61F 5/0111* (2013.01)

(58) Field of Classification Search
CPC ....... A43B 1/0081; A43B 7/20; A43B 13/203; A43B 23/029; A61F 5/0111; A61F 5/0127; A61F 2/30942; A61F 2/3859; A61F 2002/30952; A61F 2/66; A61F 5/0102; A61F 13/20; A61F 13/26; A61F 2002/30617; A61F 2002/3071;
(Continued)

(56) References Cited

U.S. PATENT DOCUMENTS 4,638,794 A * 1/1987 Grisar .................... A61F 5/0111
602/27
5,503,622 A * 4/1996 Wehr .................... A61F 5/0127
128/882
(Continued)

OTHER PUBLICATIONS

International Search Report for PCT/AU2013/000655 dated Sep. 5, 2013 (4 pages).

*Primary Examiner* — Ophelia A Hawthorne
(74) *Attorney, Agent, or Firm* — K&L Gates LLP

(57) ABSTRACT

An ankle support having a leg portion connected sidewardly and rearwardly to a foot portion by at least one elongate resilient C-shaped member extending vertically on at least one medial or lateral side of an Achilles tendon of a wearer, wherein the at least one C-shaped member opens forwardly around at least one medial or lateral malleoli of the wearer, and wherein the at least one C-shaped member is constructed and arranged to allow natural functional ankle movement in both dorsiflexion and plantar flexion with minimal impedance while controllably inhibiting rolling ankle movement in inversion or eversion.

8 Claims, 23 Drawing Sheets

(58) Field of Classification Search
CPC ...... A61F 2250/0059; A61F 2250/0067; A61F 2002/6614; A61F 2002/6678; A61F 2/6607; A61F 2002/30329; A61F 2002/30464; A61F 2002/5079; A61F 2002/607; A61F 2002/608; A61F 2002/665; A61F 13/064; A61F 2/105; A43C 1/00; A43C 11/00; A47C 9/002; A61B 2562/0247; A61B 2562/0261; A61B 5/1036; A61B 5/112; A61B 5/68
USPC .......................................... 602/23–28, 60–62
See application file for complete search history.

(56) References Cited

U.S. PATENT DOCUMENTS

| | | | | |
|---|---|---|---|---|
| 5,944,678 | A | * | 8/1999 | Hubbard ............... A61F 5/0111 602/27 |
| 2011/0034846 | A1 | | 2/2011 | Draper |
| 2011/0104968 | A1 | * | 5/2011 | Johnson ................ A63B 31/12 441/60 |

\* cited by examiner

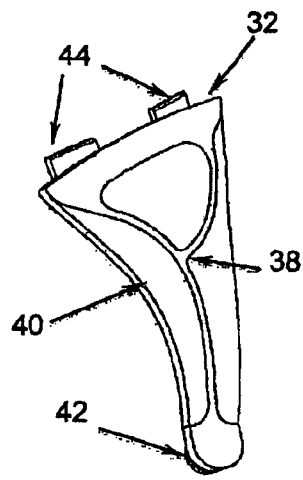
Figure 11
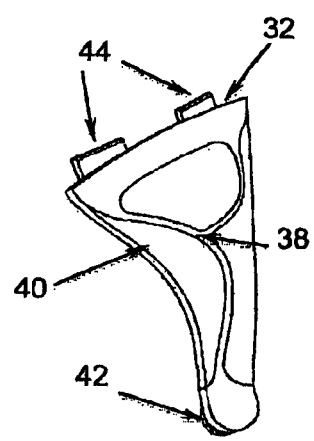
Figure 12
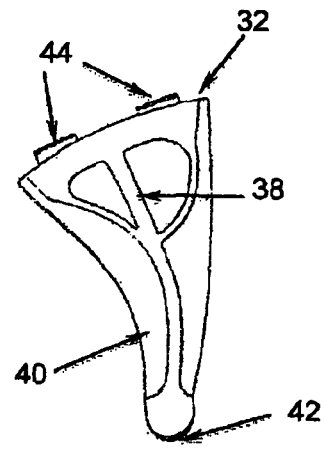
Figure 13
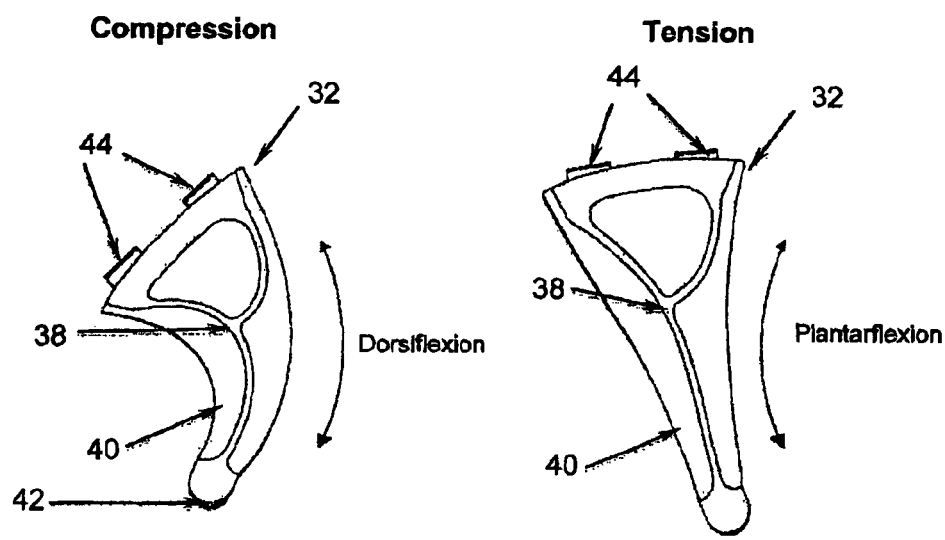
Compression
Tension
Figure 14
Figure 15

ANKLE SUPPORTS

This application is the U.S. National Stage filing under 35 U.S.C. §371, of the International Application No. PCT/AU2013/000655, entitled ANKLE SUPPORTS, filed Jun. 19, 2013, which designates the U.S., is published in English, and claims priority under 35 U.S.C. §§119 or 365(c) to Australian Patent Application No. 2012902571, filed Jun. 19, 2012, the entire disclosures of which are hereby incorporated by reference herein.

FIELD

The present invention relates to ankle supports (or braces) for sports, work and recreational activities.

BACKGROUND

Ankle braces and adhesive sports tape are commonly used to provide ankle support and prevent or minimise ankle ligament injuries in sports, work and recreational activities. Conventional hinged or wrap ankle braces typically provide static lateral stability but hinder dynamic sports performance by unduly restricting natural range of ankle motion.

Adhesive sports tape typically provides proprioception (or perception of support) but is difficult to apply, not reusable, loosens due to perspiration and causes skin irritation.

A need therefore exists for ankle supports that address or alleviate at least some of the problems described above.

SUMMARY

According to the present invention, there it provided an ankle support having a leg portion connected sidewardly and rearwardly to a foot portion by at least one elongate resilient C-shaped member extending vertically on at least one medial or lateral side of an Achilles tendon of a wearer, wherein the at least one C-shaped member opens forwardly around at least one medial or lateral malleoli of the wearer, and wherein the at least one C-shaped member is constructed and arranged to allow natural functional ankle movement in both dorsiflexion and plantar flexion with minimal impedance while controllably inhibiting rolling ankle movement in inversion or eversion.

The leg portion may be connected sidewardly and forwardly to the foot portion by at least one resilient stay.

The ankle support may have medial and lateral sides, wherein both the at least one C-shaped member and the at least one resilient stay are provided on the lateral side of the ankle support.

The at least one resilient stay may be removably connectable between the leg portion and the foot portion.

The at least one resilient stay may include a spine of resilient, semi-rigid material.

The spine may be at least partially surrounded by a skin of conformable, flexible material.

The spine may be generally Y-shaped or generally X-shaped with a plurality of branch members, wherein at least one branch member is sacrificial by being adapted to break before other branch members.

The present invention also provides an article of footwear including an ankle support described above.

BRIEF DESCRIPTION OF DRAWINGS

Embodiments of the invention will now be described by way of example only with reference to the accompanying drawing, in which:

FIGS. 11 to 13 are front views of mutually different configurations of the resilient stay;

FIGS. 14 and 15 are front views of the resilient stay in dorsiflexion and plantarflexion respectively;

DESCRIPTION OF EMBODIMENTS

Figure 2:
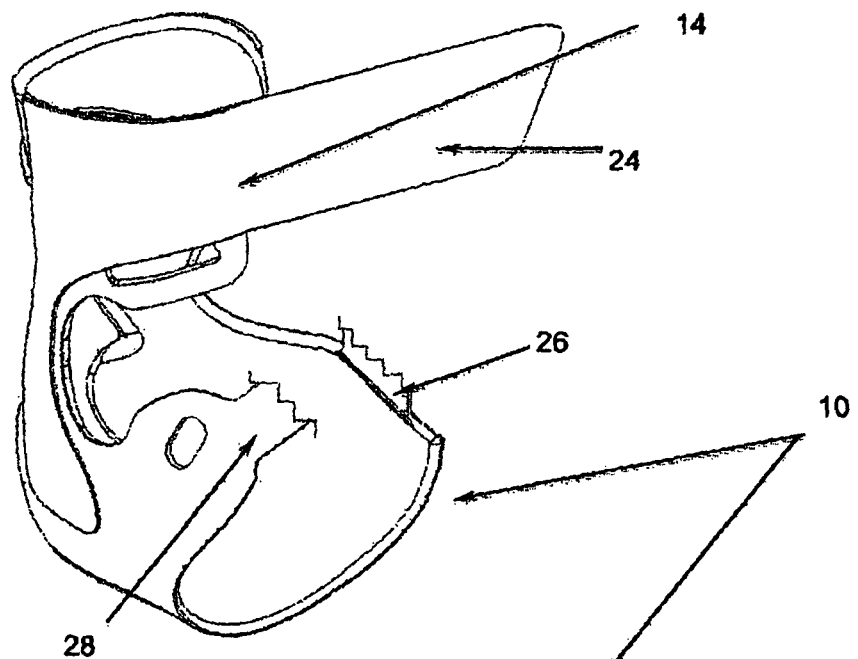
FIG. 2 is a front perspective view of a skin for the skeleton of FIG. 1.
Figure 1:
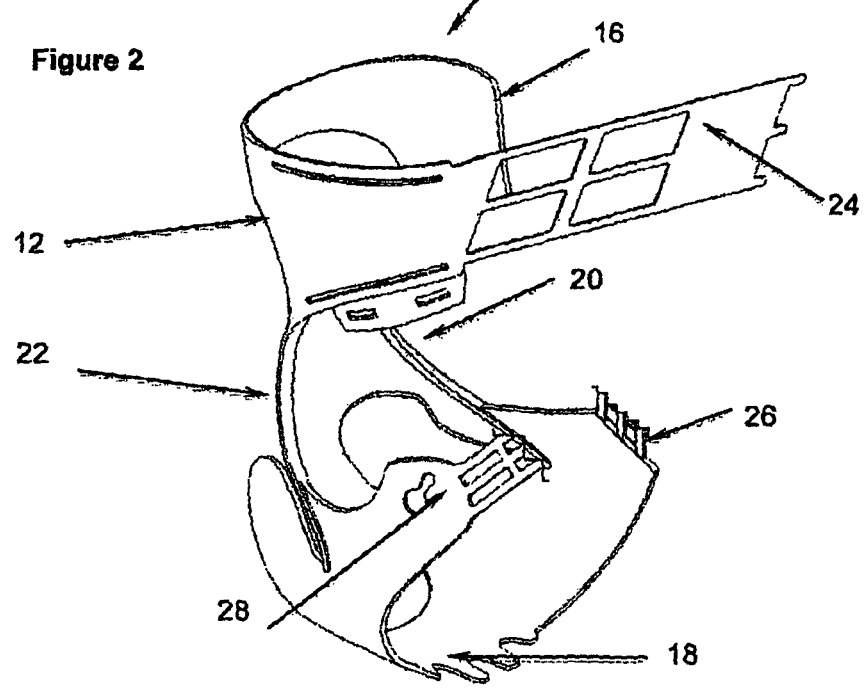
FIG. 1 is a front perspective view of a skeleton of an ankle support having medial and lateral C-shaped members according to one embodiment of the present invention.
Figure 18:
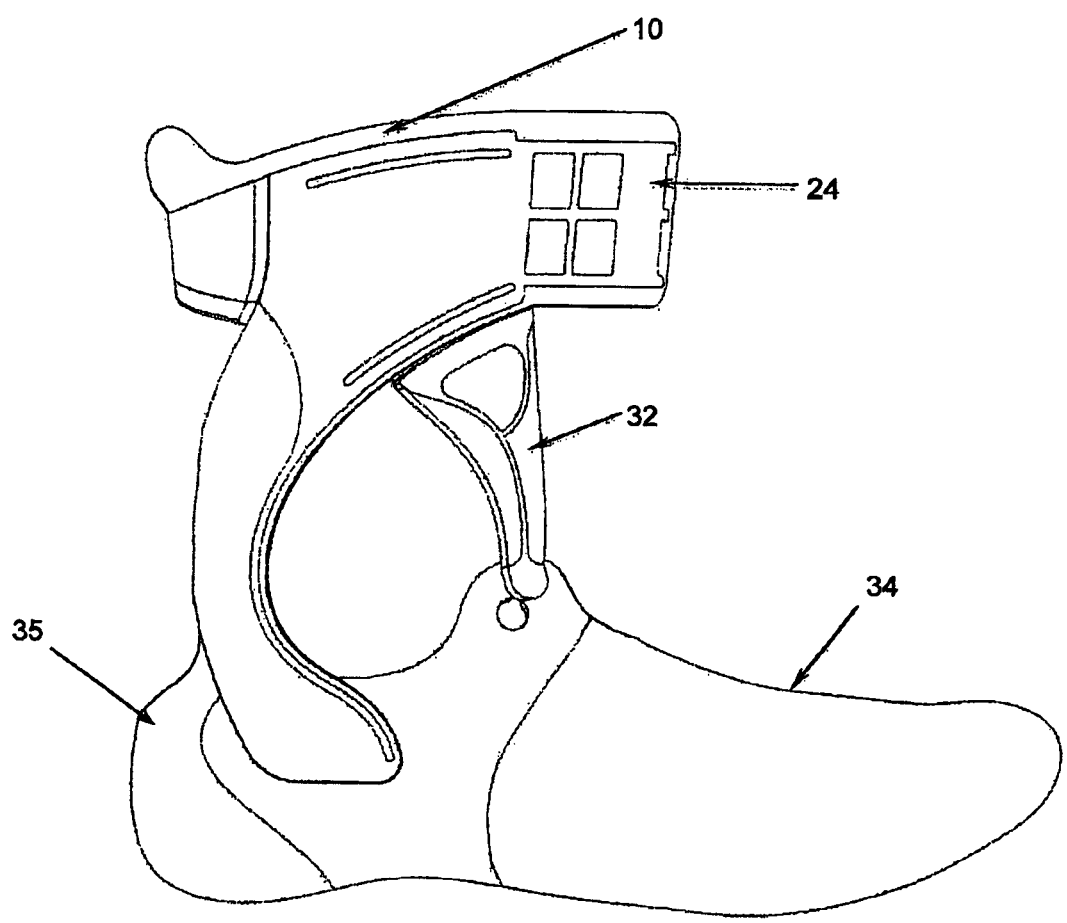
FIG. 18 is a side view of the ankle support integrated with a bootie insert for a boot.
Figure 32:
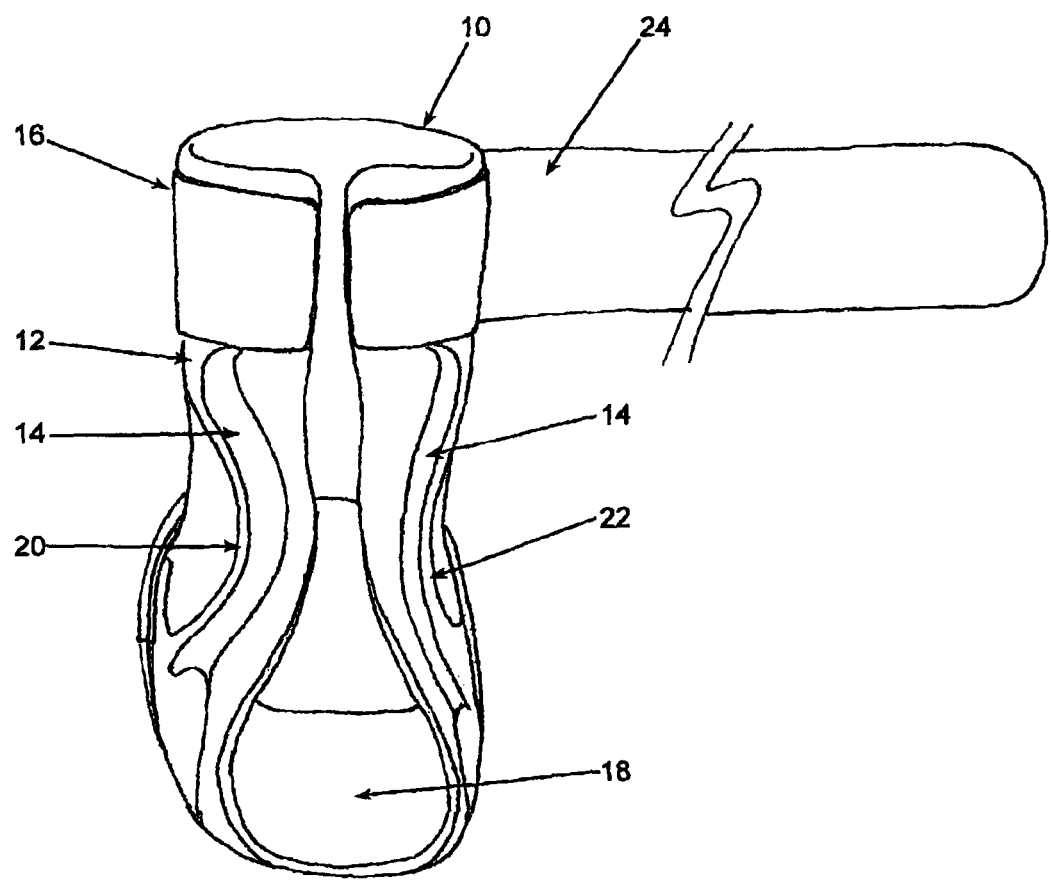
FIG. 32 is a rear view of the ankle support of FIGS. 21 to 27.

FIGS. 1 to 4 illustrate an ankle support 10 according to a first embodiment of the present invention. Referring to FIGS. 1 and 2, the ankle support 10 generally includes a skeleton 12 of a resilient, semi-rigid material, such as glass reinforced polypropylene, and a skin 14 of conformable, flexible material, such as thermoplastic polyester elastomer. The skin 14 conforms and passively adheres to the skin of a wearer to provide increased proprioceptive stimuli, feedback and awareness to a wearer in similar fashion to conventional adhesive sports tape. Other equivalent materials may also be used. The skeleton 12 includes a leg portion 16 connected sidewardly and rearwardly to a foot portion 18 by lateral (outside) and medial (inside) forwardly opening elongate resilient C-shaped members 20, 22. The C-shaped members 20, 22 are generally, substantially or at least partially C-shaped. Other equivalent configurations of C-shaped members or C-springs may also be used. The leg portion 16 is, for example, shaped and dimensioned as a rearwardly and/or forwardly opening cuff adapted to fit around a lower leg and allow rear and/or front insertion of the leg into the leg portion 16. The leg portion 16 is optionally formed by opposing complementary upper portions of the C-shaped members 20, 22 so that the leg portion 16 has both front and/or rear access via front and/or rear openings. For example, FIG. 32 illustrates an embodiment of the ankle support 10 having a leg portion 16 with rear access provided by a closable rear opening. The foot portion 18 is, for example, shaped and dimensioned to surround a heel of a foot, and extend across the foot arch forwardly of the heel and rearwardly of the fifth metatarsal. The foot portion 18 is, for example, generally, substantially, or at least partially U-shaped in cross section. Referring to FIG. 18, the foot portion 18 optionally includes a heel lock portion 35 that extends up and around a wearer's heel to positively and lockingly engage the heel of the foot. Other equivalent configurations of the leg portion 16 and the foot portion 18 may also be used. The leg portion 16 and the foot portion 18 are respectively adjustably attachable to the lower leg and foot via integral or removable straps 24, 26, 28 (shown in partially broken away form in FIGS. 1 and 2 for sake of clarity). The straps 24, 26, 28 are removably fastenable to the leg portion 16, foot portion 18 and one another by releasable fasteners, such as hook-and-loop strips, and structural anchor slots and loops. Other equivalent strap and fastening configurations may also be used.

Figure 3:
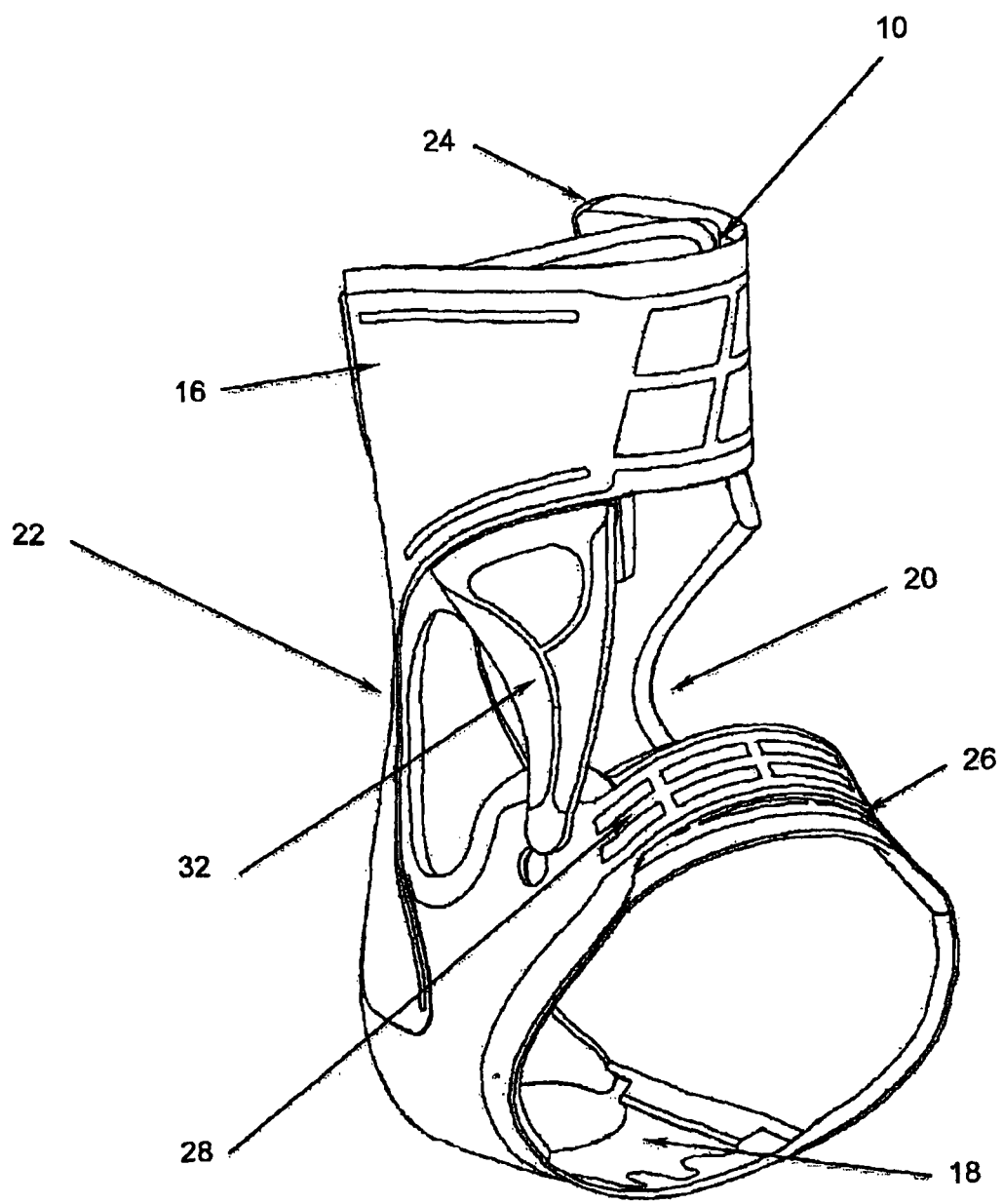
FIG. 3 is a front perspective view of the ankle support.
Figure 4:
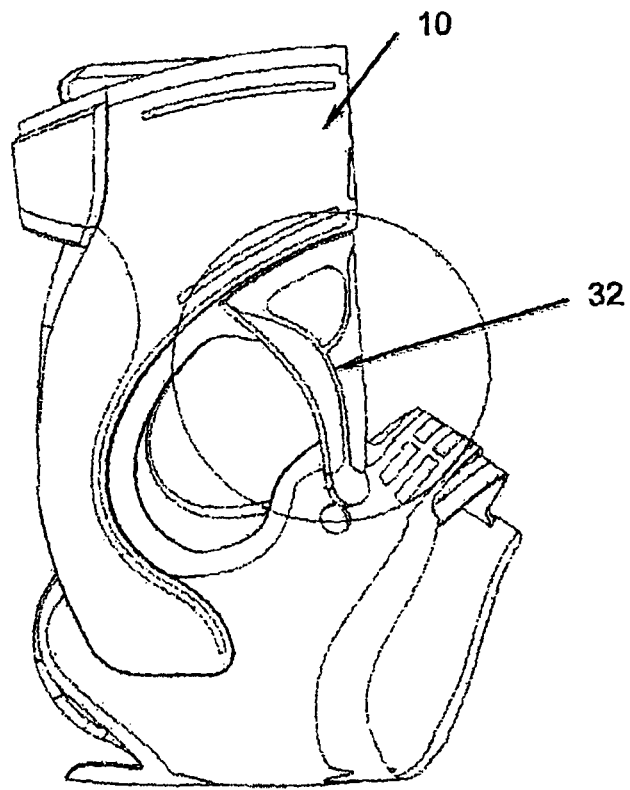
FIG. 4 is a lateral side view of the ankle support.
Figure 7:
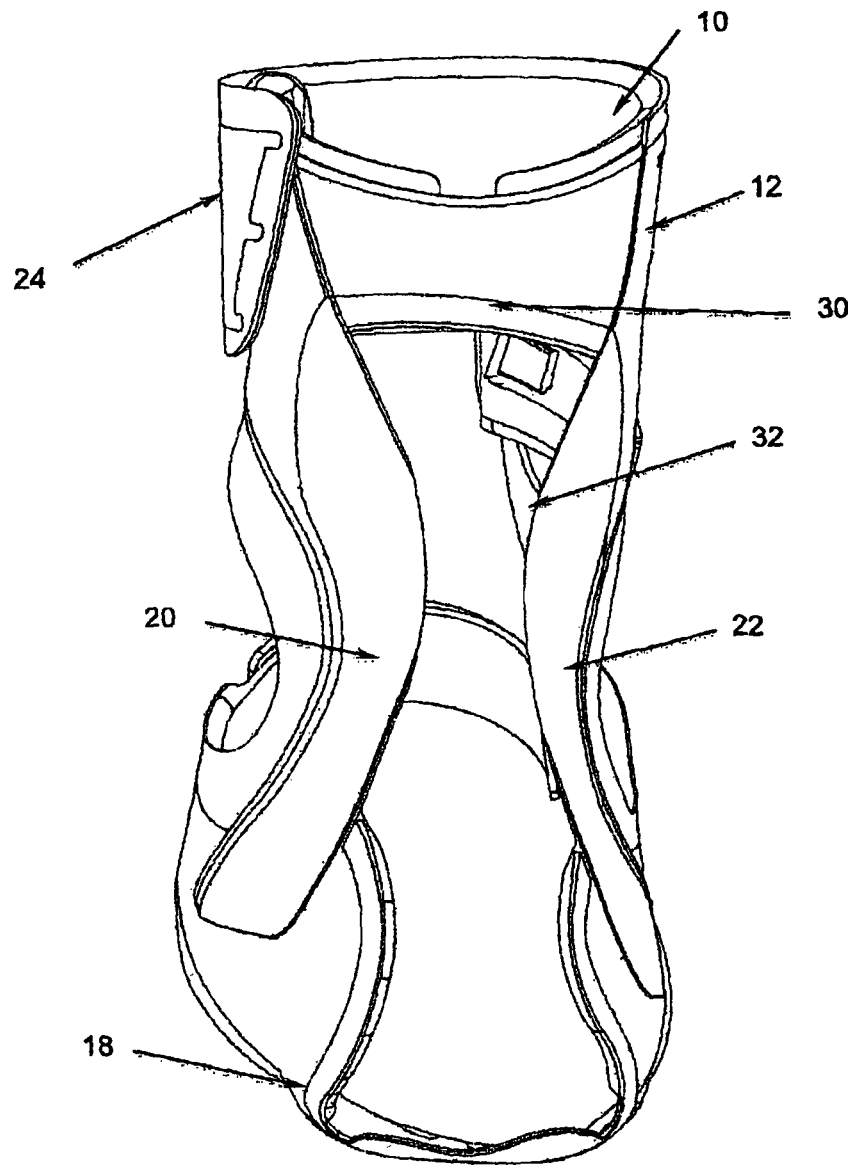
FIG. 7 is a rear view of the ankle support in a neutral position.

Referring to FIGS. 3 and 4, the skin 14 is formed over inner and outer surfaces, and around peripheral edges, of the skeleton 12 by over-moulding or co-moulding to form the complete ankle support 10. Other equivalent composite or integral construction techniques may also be used. Referring to FIG. 7, the leg portion 16 includes a spacer 30 optional formed as part of the skin 14. The C-shaped members 20, 22 are positionable on opposite medial and lateral sides of the Achilles tendon, and the spacer 30 is positionable above the Achilles tendon. The C-shaped members 20, 22 are constructed and arranged to allow natural functional ankle movement in both dorsiflexion and plantar flexion with minimal impedance while inhibiting rolling ankle movement in inversion. In other words, the shape and configuration of the C-shaped members 20, 22 are selected to controllably deform elastically in all three planes of motion of the ankle and foot (frontal, sagittal and horizontal) to allow natural functional ankle movement in plantarflexion (sagittal plane) while controllably limiting rolling ankle movement in inversion (frontal plane) and adduction (horizontal plane). The C-shaped members 20, 22 therefore provide ankle support and inhibit ankle injury by controlling supination of the foot. Supinantion is a tri-planar motion that involves inversion, adduction and plantar flexion of the foot and ankle. Although primarily concerned with preventing inversion which is the most common form of ankle injury, the ankle support 10 optionally further or alternatively provides controlled ankle movement in eversion.

To further inhibit, prevent or minimise inversion (or supination) sprains of the ankle (not shown), the leg portion 16 is connected sidewardly and forwardly to the foot portion 18 on the lateral (or outer) side of the ankle support 10 by an elongate resilient stay 32. The resilient stay 32 is removably connectable between the leg portion 16 and the foot portion 18, for example, by integral press-fit, friction-fit, slide-fit, or keyhole connectors. Although not shown, the ankle support 10 optionally further or alternatively includes a resilient stay 32 on the medial (or inner) side to prevent or minimise eversion of the ankle.

Figures 5, 6:
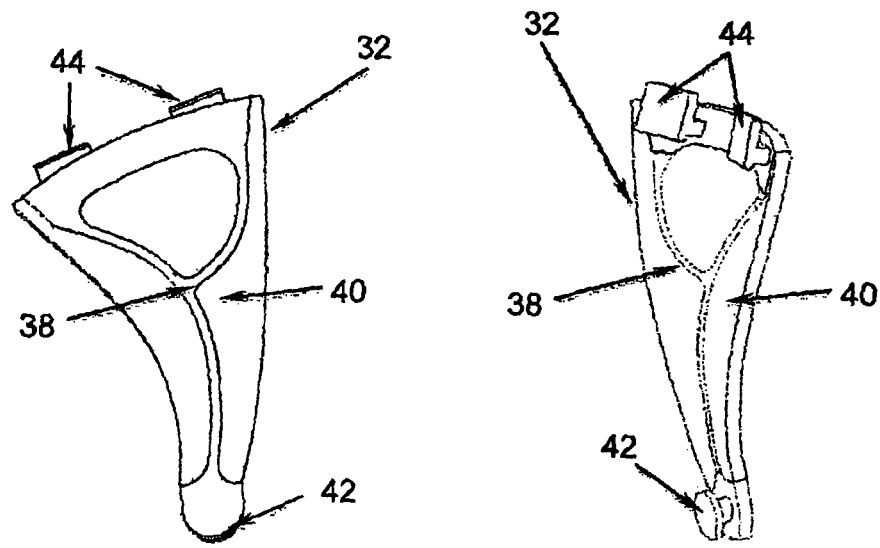
FIG. 5 is a front view of a resilient stay of the ankle support.
FIG. 6 is a rear perspective view of the resilient stay.

Referring to FIGS. 5 and 6, the resilient stay 32 includes a generally Y-shaped spine 38 of resilient, semi-rigid material, such as such as glass reinforced polypropylene, and a skin 40 of conformable, flexible material, such as thermoplastic polyester elastomer. Other equivalent materials may also be used. The Y-shaped spine 38 includes a central curved member having one sacrificial branch member adapted to break before the central curved member. FIG. 13 illustrates a trident-shaped resilient stay 32 having two sacrificial branch members adapted to break before the central curved member. The upper end of the spine 38 is provided with tabs 44 that press fit into complementary slots formed in a lower front edge of the leg portion 16. The lower end of the spine 38 is provided with a mushroom head 42 that is pivotally received in a complementary keyhole slot formed in an upper front edge of the foot portion 18.

Figure 8:
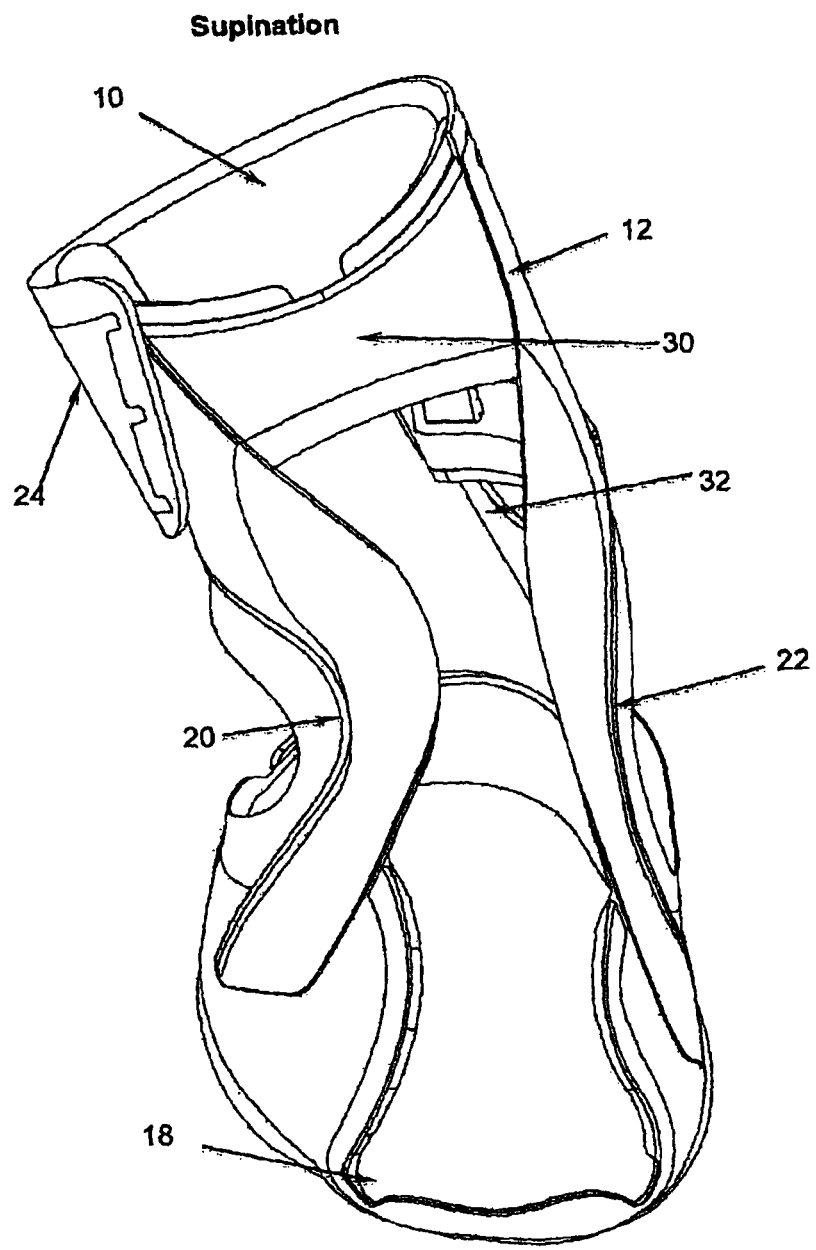
FIG. 8 is a rear view of the ankle support in supination (or inversion)
Figure 9:
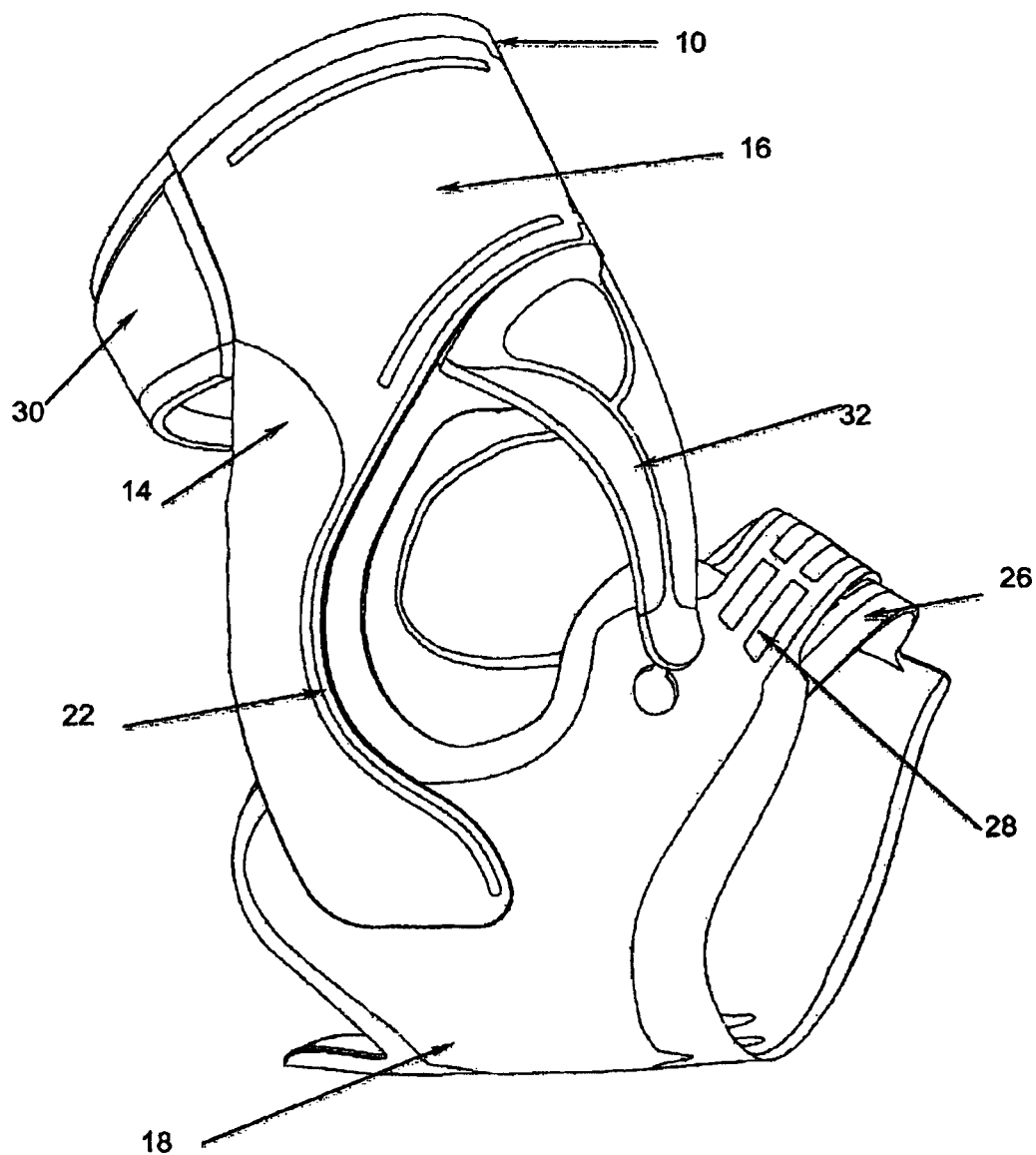
FIG. 9 is a lateral side view of the ankle support in supination and plantarflexion.
Figure 10:
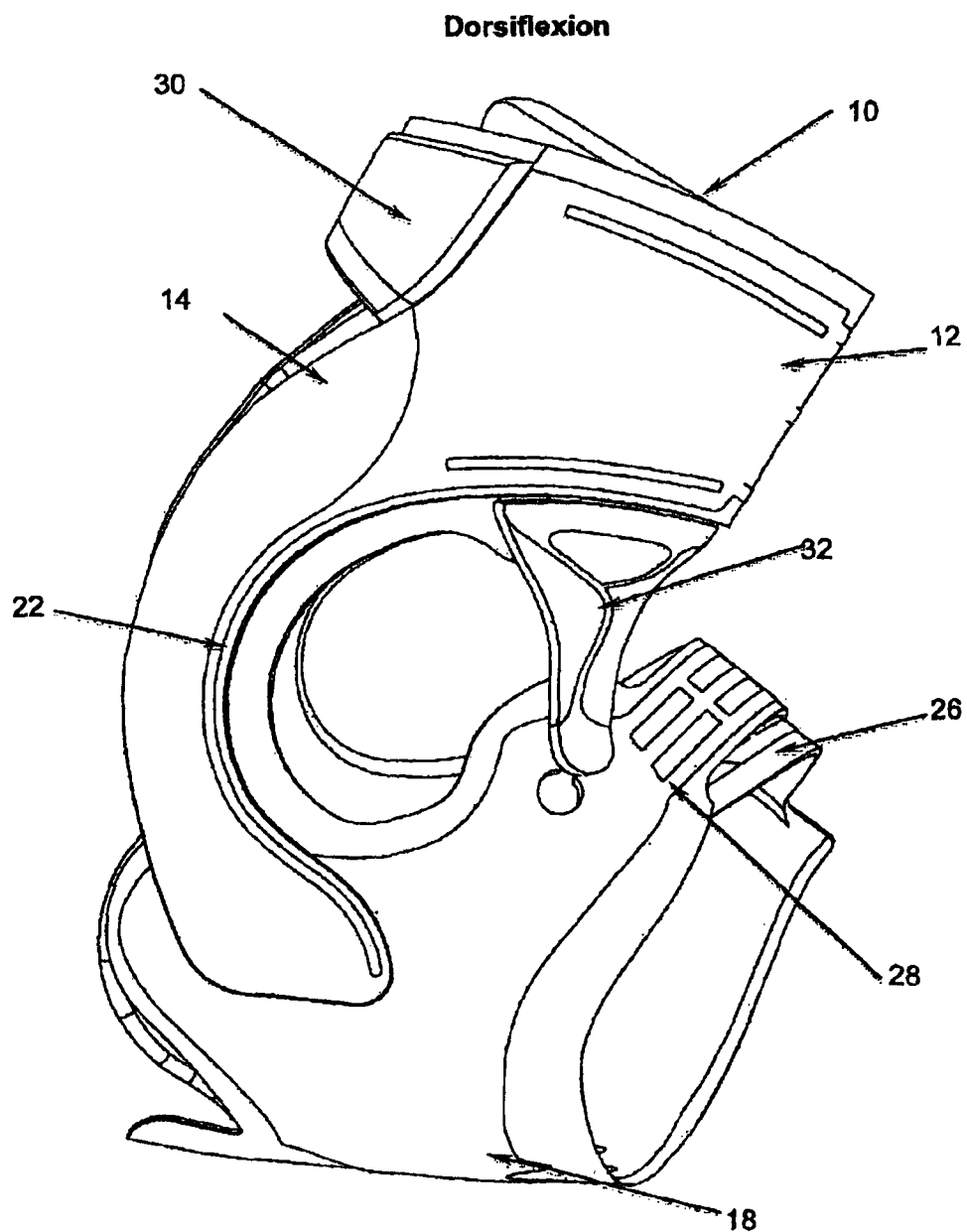
FIG. 10 is a lateral side view of the ankle support in dorsiflexion.

Referring to FIGS. 8 to 10, the medial and lateral C-shaped members 20, 22 and the lateral resilient stay 32 flex, twist and compress to allow natural range of ankle motion in plantar flexion, dorsiflexion and eversion while resiliently controlling and resisting potentially injurious range of motion in inversion. FIGS. 14 and 15 respectively illustrate compression and tension of the resilient stay 32 during dorsiflexion and plantarflexion. The central curved member of the spine 38 opens rearwardly to bias the resilient stay 32 towards compression during dorsiflexion. During plantarflexion, the central curved member of the spine 38 straightens and elongates under tension.

Referring to FIGS. 11 to 13, a plurality of mutually different resilient stays 32 are optionally interchangeable to provide different levels of inversion resistance. For example, FIGS. 11 and 12 respectively illustrate resilient stays 32 having long and short spines 38, wherein the short spine 38 provides greater inversion resistance relative to the long spine 38. The degree of inversion resistance provided by different resilient stays 32 is optionally varied by selecting mechanical properties of materials of the spine 38 and skin 40 to provide different tensile strengths, durometers, elasticities and resiliencies. Further or alternatively, the cross section area and shape of the spine 38 are selectively varied to provide resilient stays 32 with mutually different rigidities, resiliencies, tensile strengths and elasticities for different degrees of inversion resistance. The mechanical properties of the C-shaped members 20, 22 are optionally selectively varied in a similar fashion.

Figure 16:
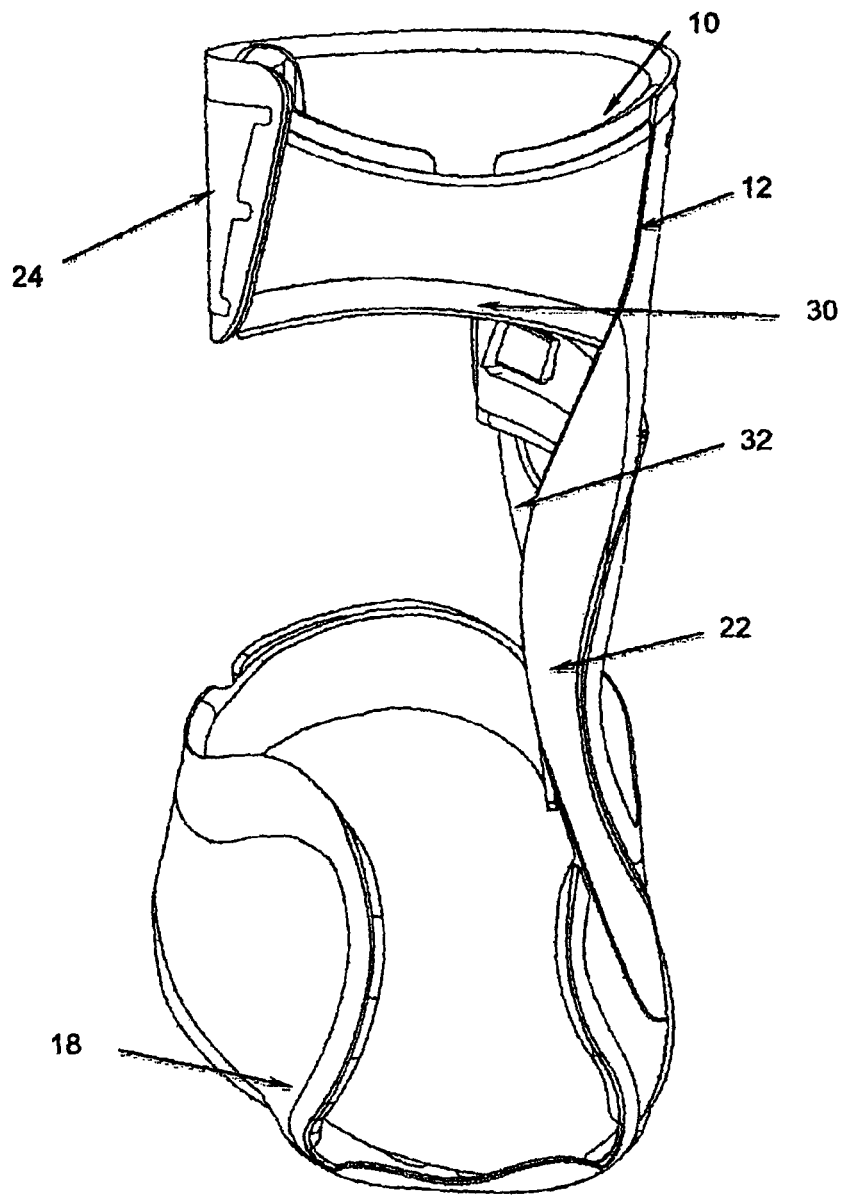
FIG. 16 is a rear view of an ankle support having a lateral C-shaped member according to another embodiment of the present invention.

Referring to FIG. 16, a second embodiment of the ankle support 10 omits the medial C-shaped member 20 so that ankle support and inversion resistance is provided by the lateral C-shaped member 22 and lateral resilient stay 32. Other equivalent combinations of lateral and/or medial C-shaped members, and lateral and/or medial resilient stays, may also be used.

Figure 17:
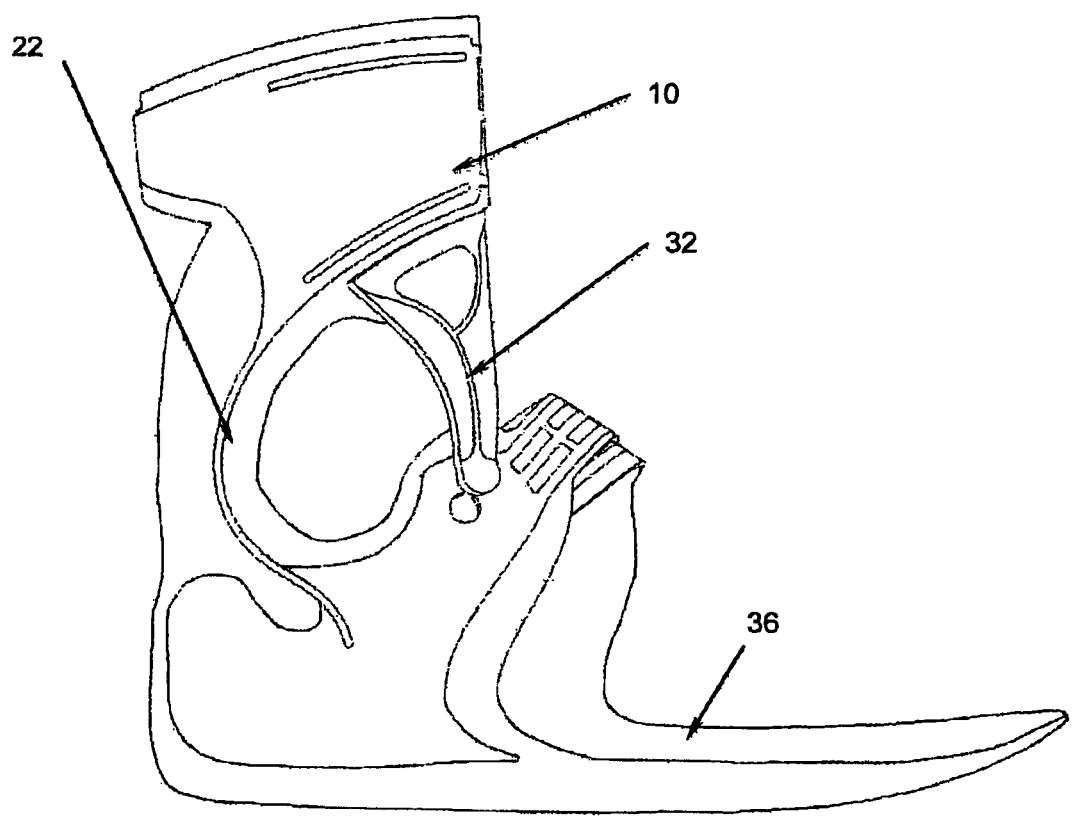
FIG. 17 is a side view of the ankle support integrated with a footwear insole.
Figure 19:
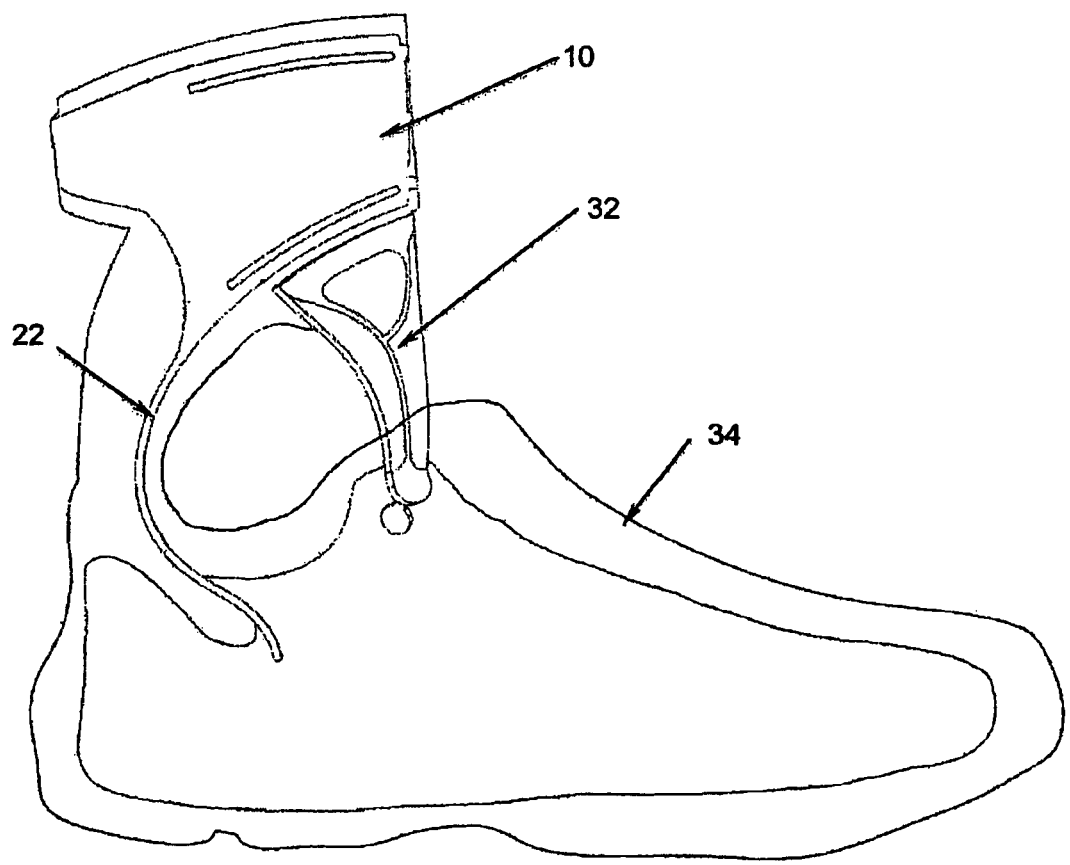
FIG. 19 is a side view of the ankle support integrated into a sports shoe.

The thicknesses of the skeleton 12 and the skin 14 are selected so that the ankle support 10 is sufficiently low profile to be removably received, or wholly or partially integrated internally or externally, in an article of footwear. The ankle support 10 can therefore be worn inside or outside a sock inside a normal shoe or boot. For example, FIG. 17 illustrates the ankle support 10 integrated in with a footwear insole 36. FIG. 18 illustrates the ankle support 10 integrated with a bootie insert 34 for a boot, such as motocross boot (not shown). FIG. 19 illustrates the ankle support 10 integrated into articles of sports footwear, such as running shoes, football boots, basketball shoes, etc. Further or alternatively, the ankle support 10 is optionally integrated in work footwear, such as work boots, to enhance occupational health and safety by reducing workplace ankle inversion injuries.

Figure 20:
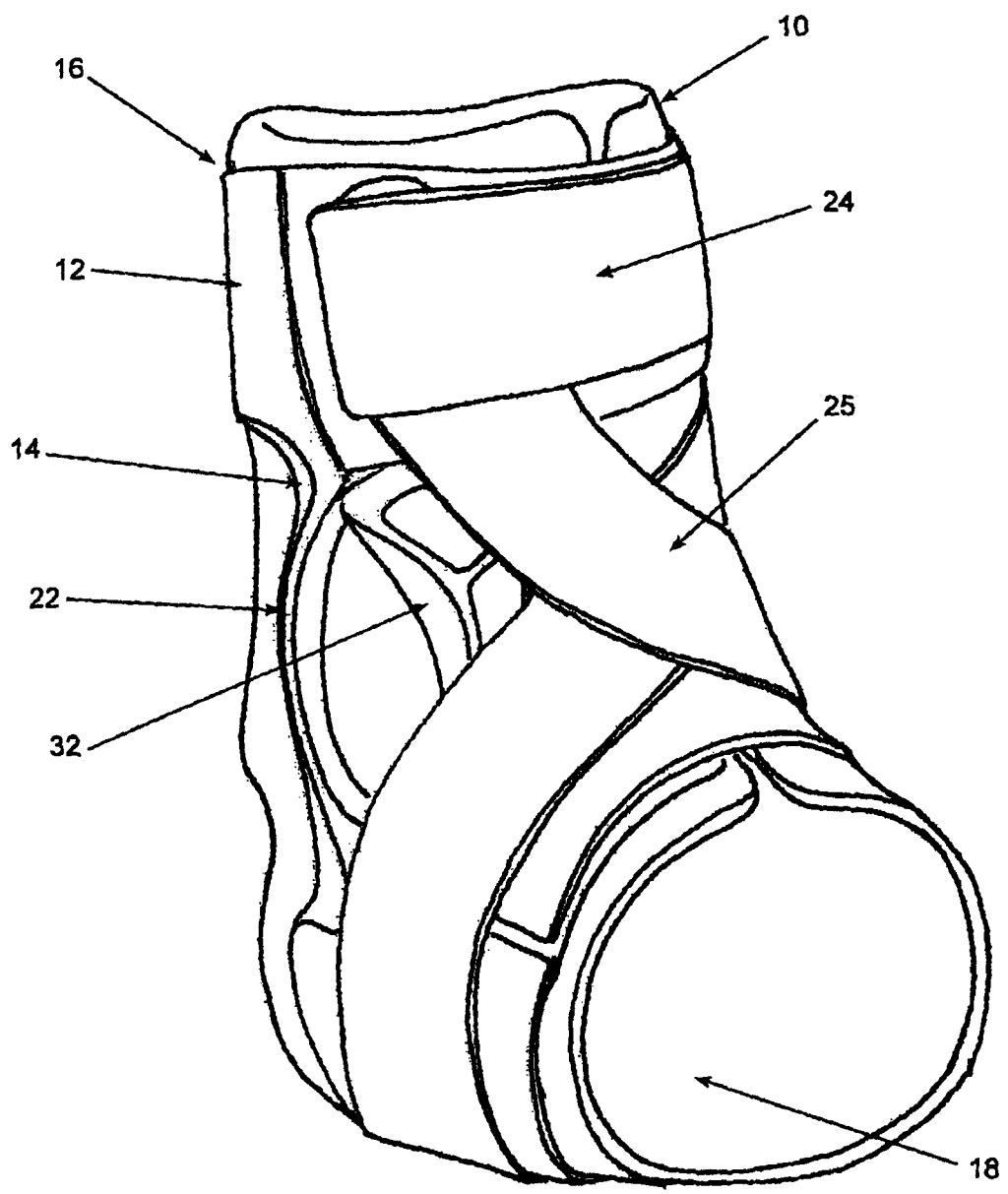
FIG. 20 is a front perspective view of a further embodiment of the ankle support having a figure-of-eight shaped attachment strap.
Figure 21:
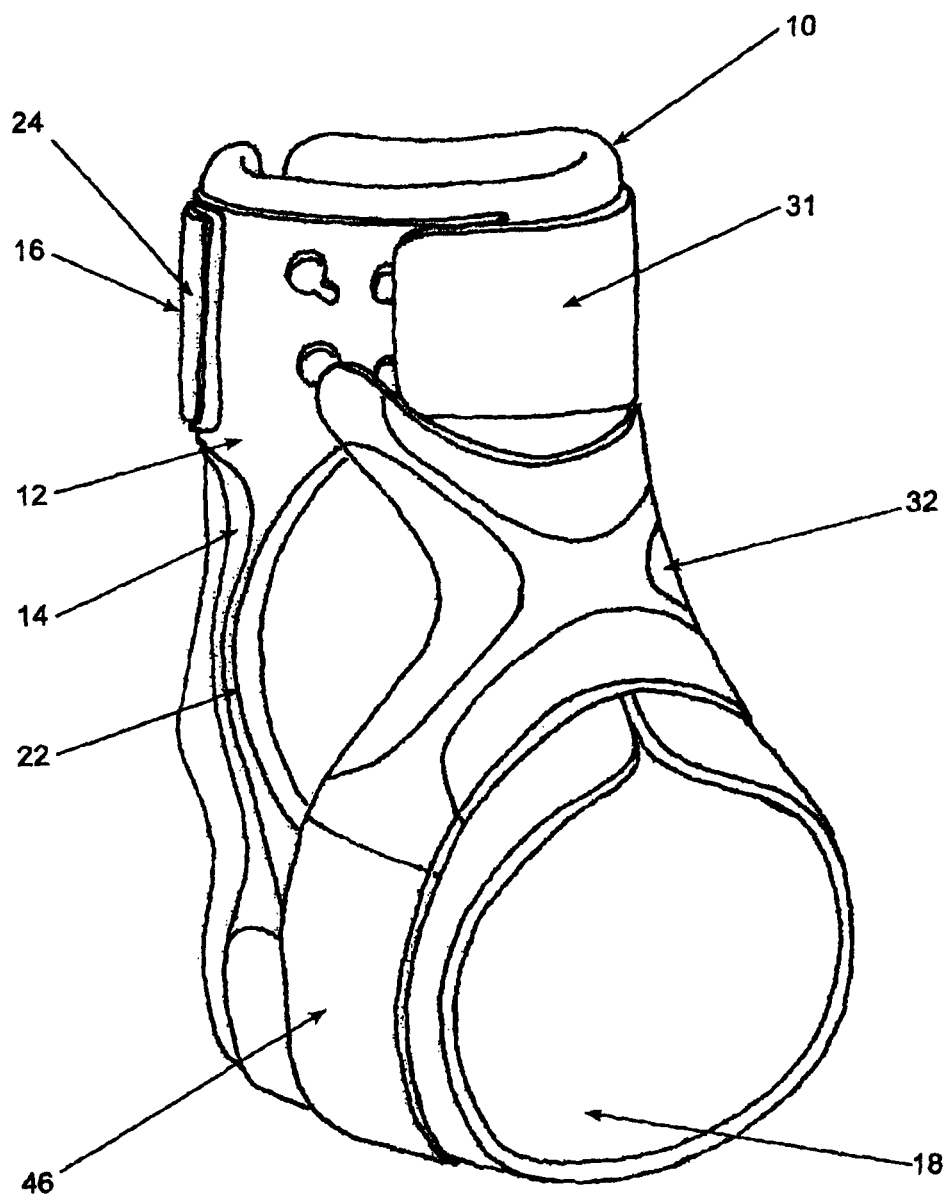
FIGS. 21 to 27 are front and rear perspective views another embodiment of the ankle support having an X-shaped resilient stay in the neutral position, and during supination, plantarflexion, dorsiflexion, and combinations thereof.

FIG. 20 illustrates a further embodiment of the ankle support 10 in which attachment straps 24, 25, 26 are integrated into a generally X-shaped, cross-over, wrap-around, or figure-of-eight shaped strap 24, 25, 26. The figure-of-eight shaped strap 24, 25, 26 extends under and around the foot portion 18, crosses over itself in front of the leg and above the foot, and then wraps around to close the leg portion 16. The figure-of-eight shaped strap 24, 25, 26 is optionally at least partially resilient and self-fastenable onto itself, for example, by releasable fasteners, such as low-profile or micro hook-and-loop or touch strip fasteners. This strap arrangement allows the ankle support 10 to be securely and comfortably self-applied, fitted and adjusted by a wearer without prior strapping or taping knowledge or skills so that they feel 'strapped up' or 'taped up'. In addition, this strap arrangement provides a 'tape-like' feel that increases proprioceptive stimuli to prevent injurious ankle movement in inversion by giving proprioceptive information and feedback to the wearer of imminent onset of movement in inversion.

Figure 22:
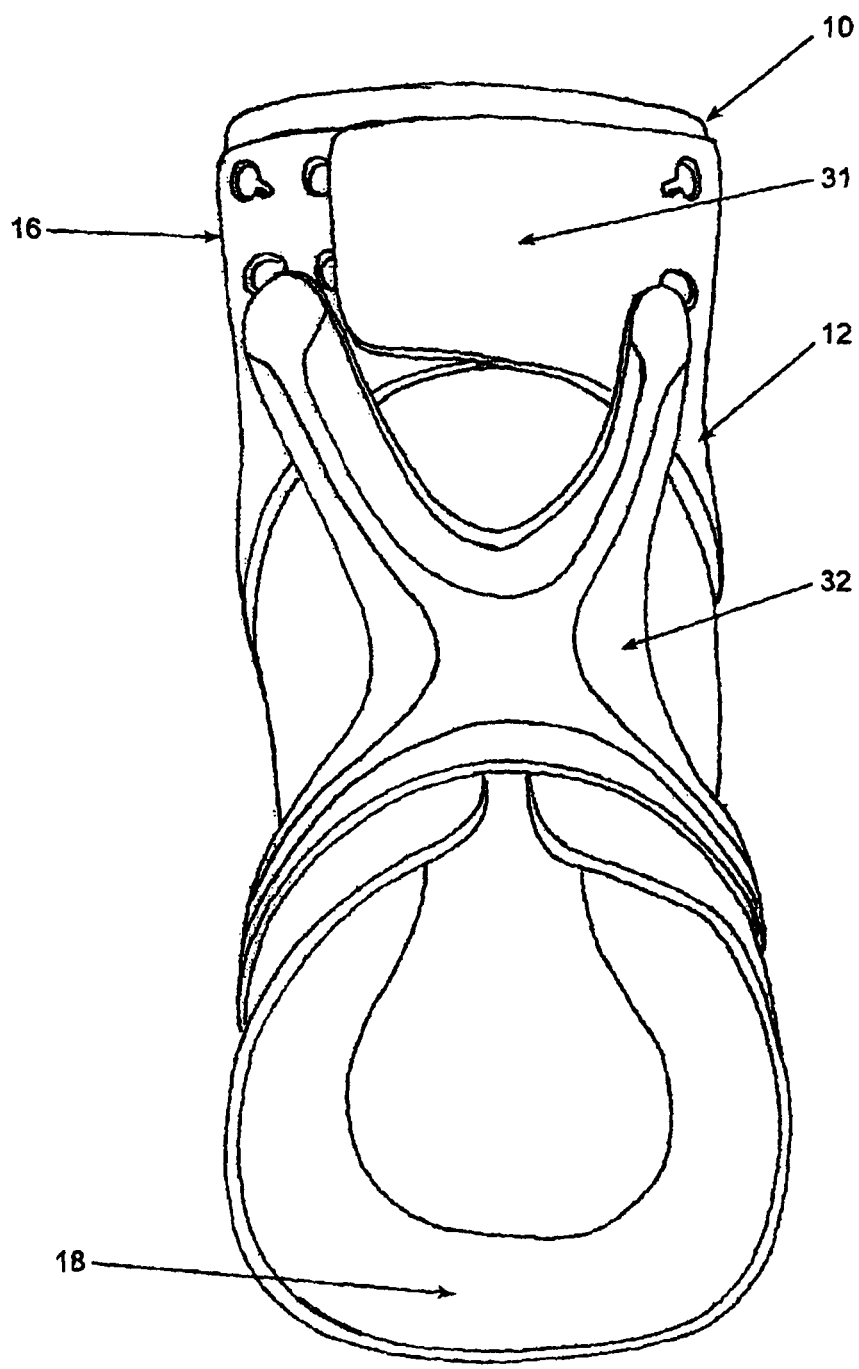
Figure 23:
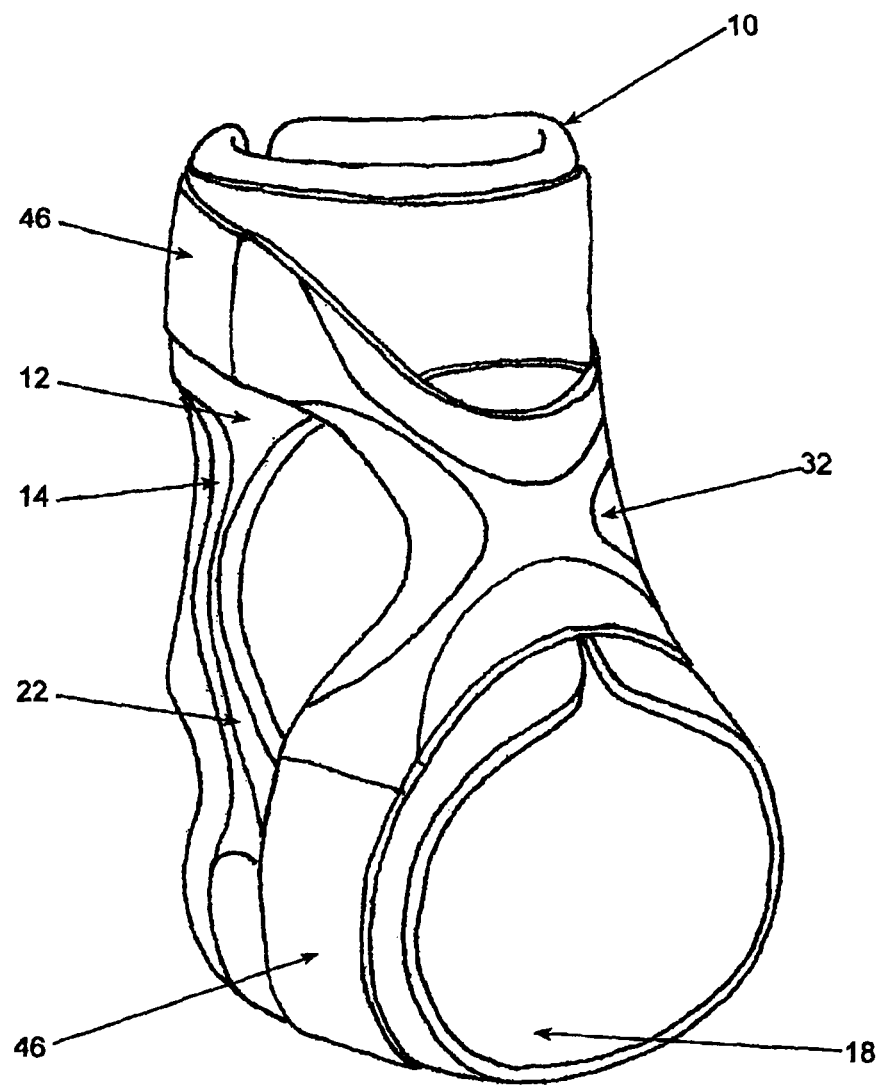
Figure 24:
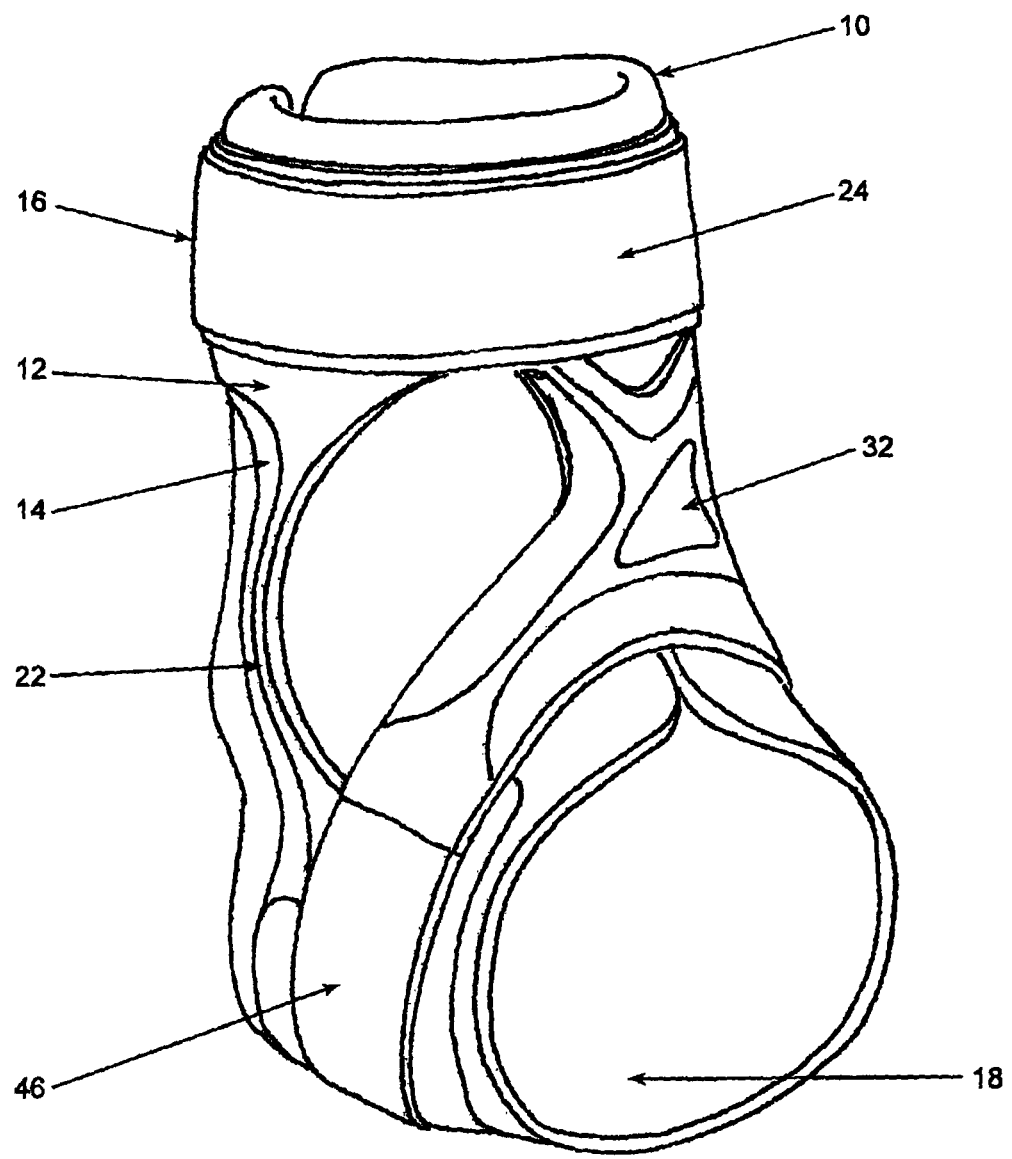
Figure 25:
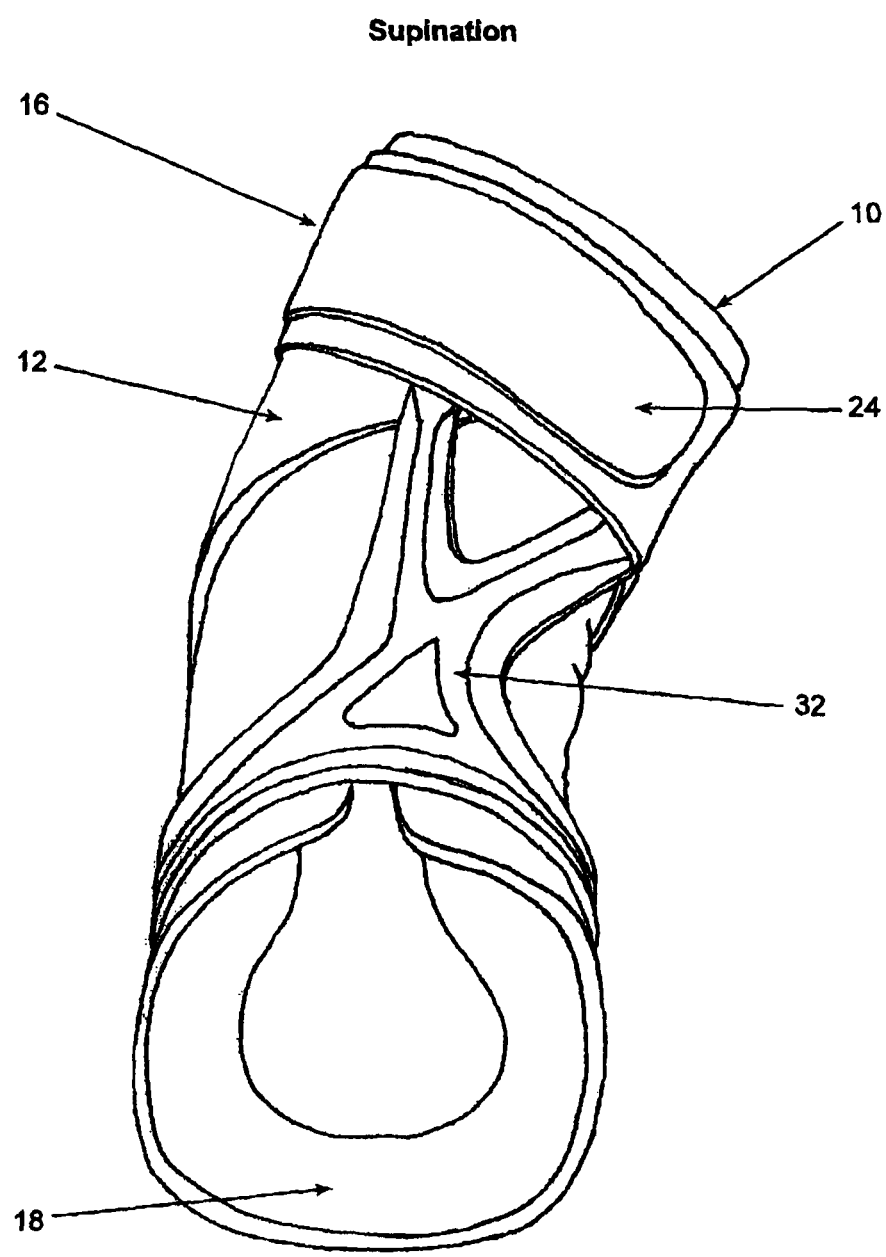
Figure 26:
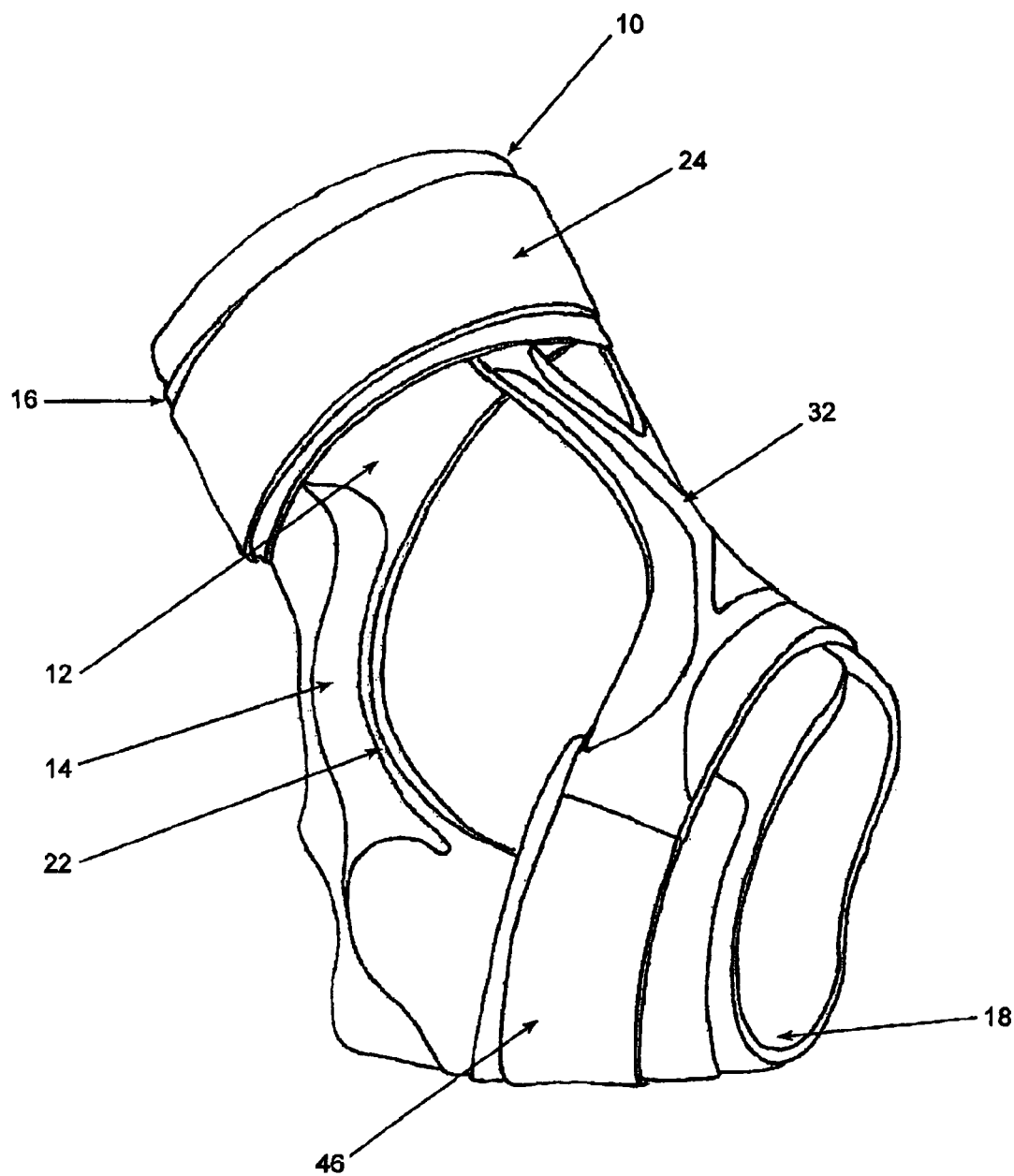
Figure 27:
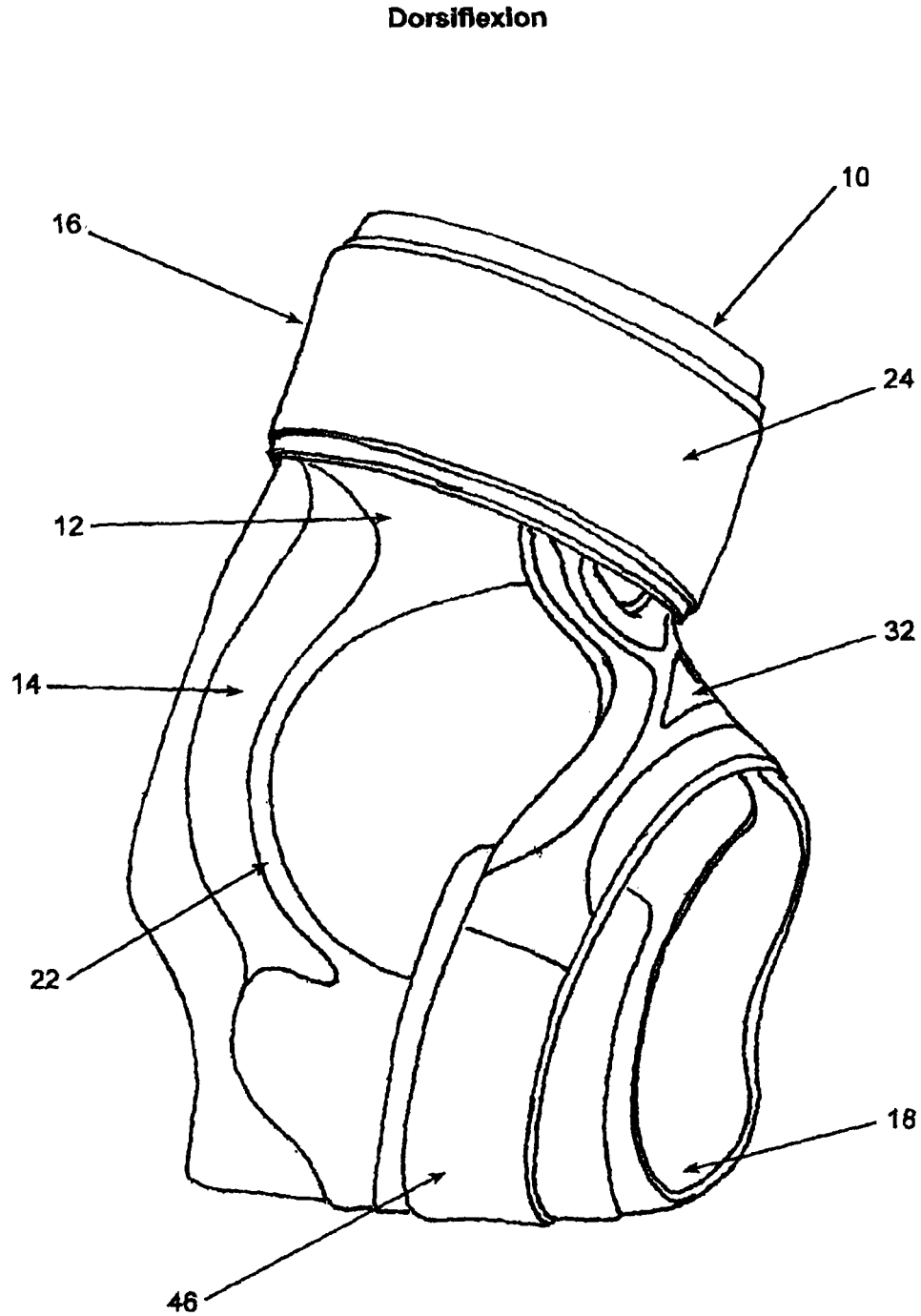
Figure 28:
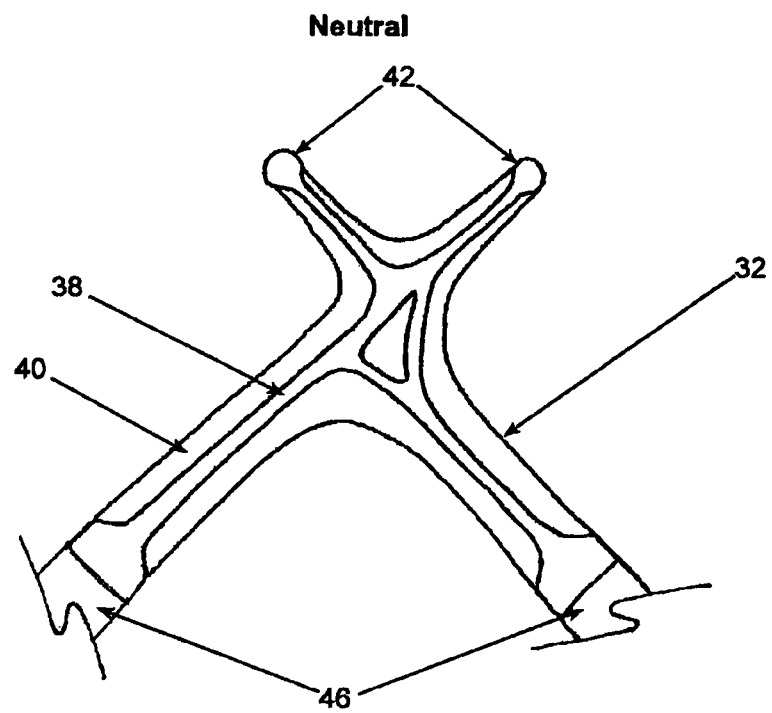
FIGS. 28 to 31 are front views of the X-shaped resilient stay in the neutral position, and during compression (dorsiflexion), extension (plantarflexion), and supination.
Figure 29:
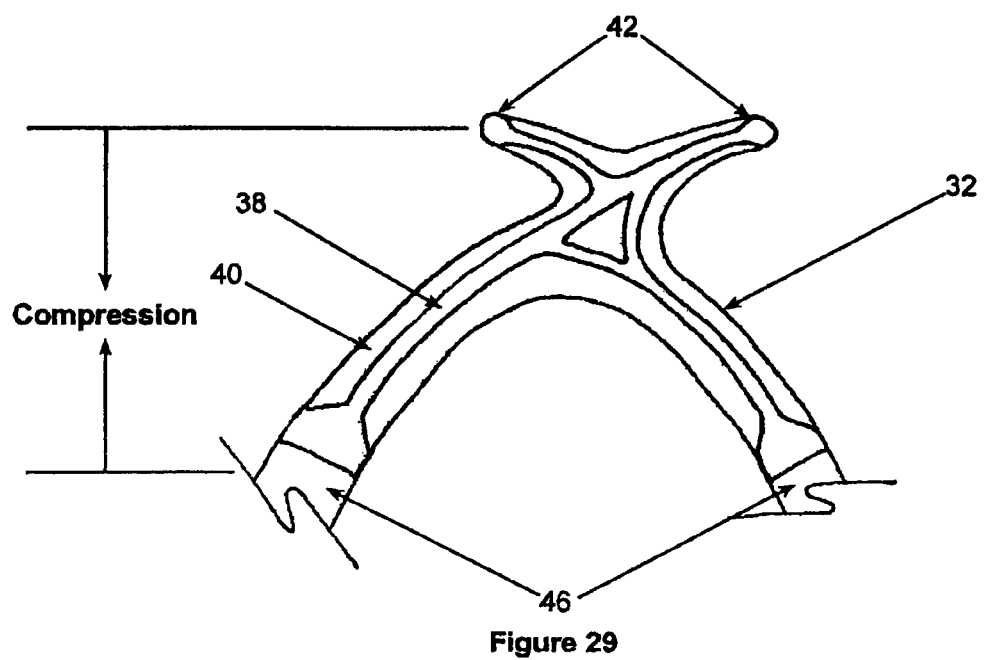
Figure 30:
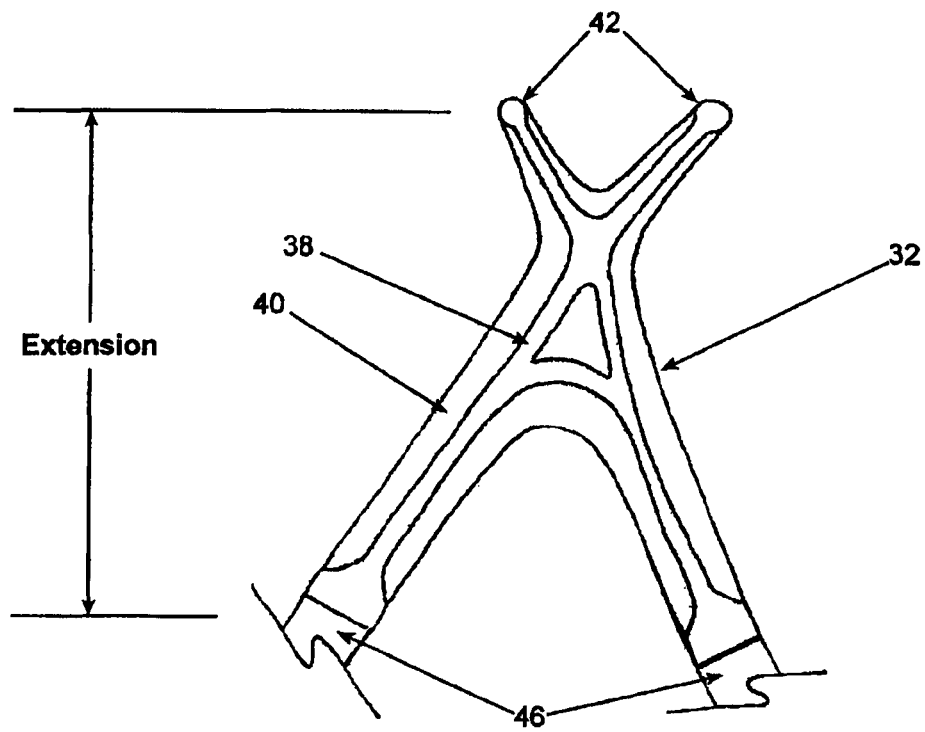
Figure 31:
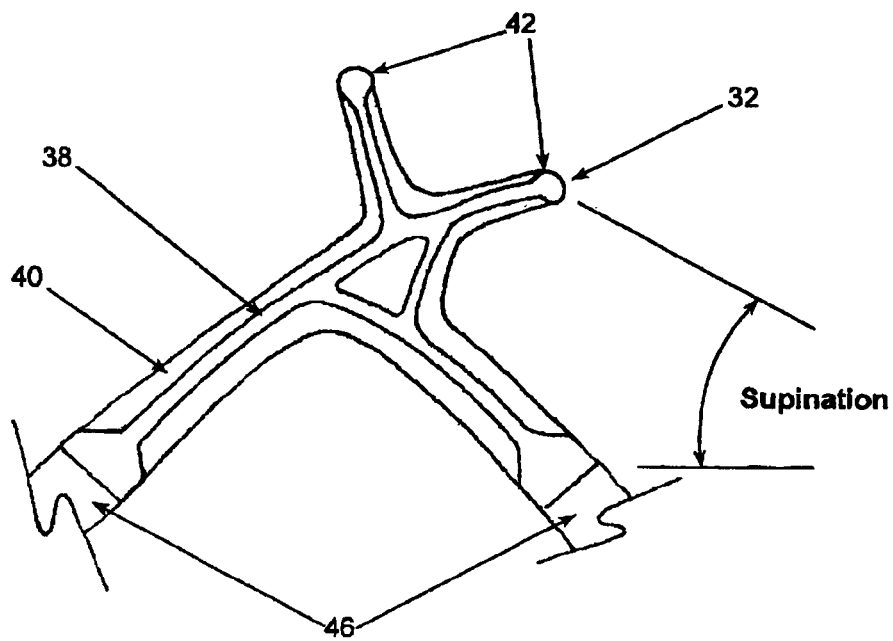

FIGS. 21 to 32 illustrate further embodiments of the ankle support 10 in which the resilient stay 32 is generally X-shaped. The lower branches of the X-shaped resilient stay 32 extend under and around the foot portion 18. The end portions of the lower branches of the X-shaped resilient stay 32 are releasably fastenable to the foot portion 18 via hook-and-loop fasteners, such as low profile hook-and-loop fasteners. Referring to FIG. 22, the upper branches of the X-shaped resilient stay 32 are optionally removably connectable to front portions of the leg portion 16 via keyhole fasteners. As illustrated in FIGS. 23 to 27 and 32, the upper branches of the X-shaped resilient stay 32 extend beyond the keyhole fasteners to wrap around and close the leg portion 16. In these embodiments, the extended end portions of the upper branches of the X-shaped resilient stay 32 are releasably fastenable to the leg portion 16 via hook-and-loop fasteners, such as low profile hook-and-loop fasteners.

Referring to FIGS. 28 to 31, the X-shaped resilient stay 32 has a generally similar construction to the elongate resilient stay 32 described above. The X-shaped resilient stay 32 includes a generally X-shaped spine 38 of resilient, semi-rigid material, such as such as glass reinforced polypropylene, and a skin 40 of conformable, flexible material, such as thermoplastic polyester elastomer. One or more upper and lower branches on medial and laterals sides of the X-shaped spine 38 are sacrificial and adapted to break during inversion movement in injurious ranges. The X-shaped spine 38 includes a central triangular cut out that facilitates controlled range and rate of movement of the upper and lower branches during tri-planar supination motion that involves inversion, adduction and plantar flexion of the foot and ankle. FIGS. 28 to 31 respectively illustrate neutral positioning, compression, tensioning, and lateral bending of the X-shaped resilient stay 32 in the neutral position, and during complex tri-planar movement involving dorsiflexion, plantarflexion, and supination of the ankle and foot.

Embodiments of the ankle support of the present invention provide a useful alternative to ankle braces and adhesive sports tape. Embodiments of the invention provide hingeless ankle supports or braces that inhibit injurious inversion of the ankle and increase proprioceptive awareness of ankle support, position and movement. In addition, embodiments of the invention allow, and minimally impede, natural functional ankle movement in plantarflexion and dorsiflexion. Embodiments of the ankle support can be self-applied without prior specialist knowledge, and can be worn inside or outside socks in conventional footwear.

The embodiments have been described by way of example only and modifications are possible within the scope of the claims that follow.

The invention claimed is:

1. An ankle support having a leg portion connected sidewardly and rearwardly to a foot portion by at least one elongate resilient C-shaped member extending vertically on at least one medial or lateral side of an Achilles tendon of a wearer, wherein the at least one C-shaped member opens forwardly around at least one medial or lateral malleoli of the wearer, wherein the at least one C-shaped member is constructed and arranged to allow natural functional ankle movement in both dorsiflexion and plantar flexion with minimal impedance while controllably inhibiting rolling ankle movement in inversion or eversion, wherein at least one of the leg portion, foot portion and at least one C-shaped member form a skeleton of resilient, semi-rigid material, and wherein the skeleton is at least partially surrounded by a skin of conformable, flexible material.

2. The ankle support according to claim 1, wherein the leg portion is connected sidewardly and forwardly to the foot portion by at least one resilient stay.

3. The ankle support according to claim 2, wherein the at least one resilient stay includes a spine of resilient, semi rigid material.

4. The ankle support according to claim 3, wherein the spine is at least partially surrounded by a skin of comfortable, flexible material.

5. The ankle support according to claim 3, wherein the spine is generally Y-shaped or generally X-shaped with a plurality of branch members, and wherein at least one branch member is sacrificial by being adapted to break before other branch members.

6. The ankle support according to claim 2, wherein the ankle support has medial and lateral sides, and wherein both the at least one C-shaped member and the at least one resilient stay are provided on the lateral side of the ankle support.

7. The ankle support according to claim 2, wherein the at least one resilient stay is removably connectable between the leg portion and the foot portion.

8. An article of footwear including the ankle support according to claim 1.

* * * * *